United States Patent [19]

Gauthier et al.

[11] 4,132,710

[45] Jan. 2, 1979

[54] [2]BENZOPYRANO[3,4-c]PYRIDINES AND PROCESS THEREFOR

[75] Inventors: Jean A. Gauthier, Montreal; Leslie G. Humber, Dollard des Ormeaux; Clara Revesz, Montreal, all of Canada

[73] Assignee: Ayerst, McKenna and Harrison, Ltd., Montreal, Canada

[21] Appl. No.: 752,654

[22] Filed: Dec. 20, 1976

[51] Int. Cl.$^2$ .................................... C07D 491/04
[52] U.S. Cl. .................................... 546/63; 546/89; 546/115; 546/91; 546/217; 546/183
[58] Field of Search ................... 260/293.55; 424/256

[56] References Cited

U.S. PATENT DOCUMENTS

| 3,514,464 | 5/1970 | Pars et al. | 260/293.55 |
| 3,946,008 | 3/1976 | Brown et al. | 424/246 |

*Primary Examiner*—Henry R. Jiles
*Assistant Examiner*—Richard A. Schwartz
*Attorney, Agent, or Firm*—Stephen Venetianer

[57] ABSTRACT

[2]Benzopyrano[3,4-c]pyridine derivatives characterized by having a 2,3,4,4a,6,10b-hexahydro-1H-[2]benzopyrano[3,4-c]pyridine nucleus bearing a substituent at position 6 are disclosed. The nucleus can be optionally further substituted at positions 2,3,4,6 and on the aromatic ring. The derivatives are useful diuretic, anorexic, antidepressant, anticonvulsant and antihypertensive agents. Methods for their preparation and use also are disclosed.

21 Claims, No Drawings

[2]BENZOPYRANO[3,4-c]PYRIDINES AND PROCESS THEREFOR

BACKGROUND OF THE INVENTION

1. Field of the Invention

This invention relates to novel [2]benzopyrano[3,4-c]pyridine derivatives, to processes for their preparation, to methods for using the derivatives and to pharmaceutically acceptable compositions of said derivatives.

More specifically, the present invention relates to novel 2,3,4,4a,6,10b-hexahydro-1H-[2]benzopyrano[3,4-c]pyridine derivatives possessing valuable pharmacologic properties. For example, these derivatives are useful diuretic, anorexic, antidepressant, anticonvulsant and antihypertensive agents at dosages which do not elicit undesirable side effects. The combination of these pharmacologic properties with a low order of toxicity render the [2]benzopyrano[3,4-c]pyridine derivatives of the invention therapeutically useful.

2. Description of the Prior Art

A number of prior art reports dealing with benzopyrano[3,4-c]pyridines are available. For example, the [1]benzopyrano[3,4-c]-pyridine ring system is described in the German Pat. No. 2,263,100, issued July 12, 1973 and by H. G. Pars and F. E. Granchelli in the U.S. Pat. No. 3,535,327, issued Oct. 20, 1970 and U.S. Pat. No. 3,632,595, issued Jan. 4, 1972. The latter ring system is distinguished readily from the ring system of the present invention by having the oxygen function at a different position in the benzopyrano[3,4-c]pyridine nucleus and a completely different relationship between the oxygen and nitrogen atoms. Furthermore, the compounds of the present invention are distinguished from the compound of the prior art by their unique pharmacological properties.

SUMMARY OF THE INVENTION

The compounds of this invention are represented by formula I

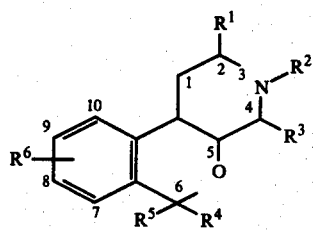

in which $R^1$ and $R^3$ are hydrogen or $R^1$ and $R^3$ together form a —(CH$_2$)$_n$— chain wherein n is an integer from 2 to 4; $R^2$ is hydrogen, lower alkyl, lower cycloalkyl(lower)alkyl, phenyl(lower)alkyl, amino(lower)alkyl, lower alkylamino(lower) alkyl or di(lower)alkylamino(lower)alkyl; $R^4$ is hydrogen or lower alkyl; $R^5$ is lower alkyl, lower cycloalkyl, phenyl or phenyl substituted with one or two substituents selected from the group consisting of nitro, halo, lower alkyl and trifluoromethyl: and $R^6$ is hydrogen, halo or lower alkyl.

Also included are the therapeutically acceptable acid addition salts of the compounds of formula I.

The novel [2]benzopyrano[3,4-c]pyridine derivatives of this formula I are prepared by condensing a compound of formula II

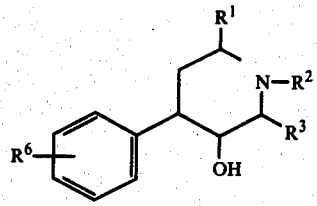

in which $R^1$, $R^3$ and $R^6$ are as defined herein and $R^2$ is lower alkyl, lower cycloalkyl(lower)alkyl or phenyl(lower)alkyl with a carbonyl compound of formula III

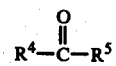

in which $R^4$ and $R^5$ are as defined herein in the presence of an acid catalyst to obtain the corresponding compound of formula I in which $R^1$, $R^3$, $R^4$, $R^5$, and $R^6$ are as defined herein and $R^2$ is lower alkyl, lower cycloalkyl(lower)alkyl or phenyl(lower)alkyl; followed, when it is desired to obtain the corresponding compound of formula I in which $R^1$, $R^3$, $R^4$, $R^5$ and $R^6$ are as defined herein and $R^2$ is hydrogen, reducing said compound of formula I in which $R^1$, $R^3$, $R^4$, $R^5$ and $R^6$ are as defined herein and $R^2$ is the phenyl(lower) alkyl, phenylmethyl, with hydrogen in the presence of a noble metal catalyst, or by reacting said compound of formula I in which $R^1$, $R^3$, $R^4$, $R^5$ and $R^6$ are as defined herein and $R^2$ is the lower alkyl, methyl, with phenyl chloroformate followed by heating with powdered sodium or potassium hydroxide; and when it is desired to obtain the compound of formula I in which $R^1$, $R^3$, $R^4$, $R^5$ and $R^6$ are as defined herein and $R^2$ is amino(lower)alkyl, lower alkylamino(lower)alkyl or di(lower)alkylamino(lower)alkyl, reacting the compound of formula I in which $R^1$, $R^3$, $R^4$, $R^5$ and $R^6$ are as defined herein and $R^2$ is hydrogen with a compound of formula ω-halo(lower)alkanoyl halide wherein each of the halogen atoms is selected from chlorine, bromine and iodine in the presence of a proton acceptor to obtain the corresponding halo-amide, reacting said halo-amide with ammonia, a lower alkylamine or a di(lower)alkylamine in the presence of a proton acceptor, to obtain the corresponding amino-amide and reducing said amino-amide with a complex metal hydride.

Another aspect of this invention involves a method for increasing the excretion of urine (diuresis) as well as suppression of appetite in a mammal which comprises administering to said mammal an effective amount of a compound of formula I, or a therapeutically acceptable salt thereof.

Still another aspect of this invention involves a method of treating depression, convulsions and hypertension in a mammal which comprises administering to said mammal an effective amount of a compound of formula I, or a therapeutically acceptable salt thereof.

Still another aspect of this invention involves a pharmaceutical composition comprising a compound of formula I, or a therapeutically acceptable salt thereof, and a pharmaceutically acceptable carrier.

DETAILED DESCRIPTION OF THE INVENTION

The term "lower alkyl" as used herein contemplates straight chain alkyl radicals containing from one to six carbon atoms and branched chain alkyl radicals containing from three to four carbon atoms and includes methyl, ethyl, propyl, isopropyl, butyl, isobutyl, pentyl, hexyl and the like.

The term "lower cycloalkyl" as used herein contemplates saturated cyclic hydrocarbon radicals containing from three to six carbon atoms and includes cyclopropyl, cyclobutyl, cyclopentyl and the like.

The term "lower alkanoyl" as used herein contemplates straight chain alkanoyl radicals containing from two to six carbon atoms and a branched chain alkanoyl radical containing four carbon atoms and includes acetyl, propionyl, isobutyryl, hexanoyl and the like.

The term "phenyl(lower)alkyl" as used herein contemplates a phenyl(lower)alkyl radical in which the alkyl portion thereof is a straight chain containing from one to six carbon atoms or a branched chain containing from two to four carbon atoms and includes benzyl, 2-phenylethyl, 2-methyl-3-phenylpropyl, 5-phenylpentyl and the like.

The term "lower cycloalkyl(lower)alkyl" as used herein contemplates a lower cycloalkyl(lower)alkyl radical in which the alkyl portion thereof is a straight chain containing from one to six carbon atoms or a branched chain containing from two to four carbon atoms and includes cyclopropylmethyl, 5-cyclobutylpentyl, 1-methyl-3-cyclopentylpropyl, 2-ethyl-2-cyclohexylethyl and the like. Thus, the lower cycloalkyl(lower)alkyl can contain 4 to 12 carbon atoms.

The term "halo" as used herein contemplates halogens and includes fluorine, chlorine, bromine and iodine, unless stated otherwise.

The term "lower alkanol" as used herein contemplates both straight and branched chain alkanols containing from one to four carbon atoms and includes methanol, ethanol, isopropanol, butanol, and the like.

Where the term "(lower)alkyl" is used in connection with the alkylene portion of the description of amino(lower)alkyl, lower alkylamino(lower)alkyl and di(lower)alkylamino(lower)alkyl, it contemplates a divalent organic radical derived from a straight chain aliphatic hydrocarbon containing from one to six carbon atoms or a branched chain aliphatic hydrocarbon containing from two to four carbon atoms and includes methylene, 2-methylpropylene, ethylene, hexylene and the like.

The term "proton acceptor" as used herein contemplates the organic bases, or amines for instance, triethylamine, pyridine, N-ethylmorphone, 1,5-diazabicyclo[3.4.0]nonene-5 and the like, as well as the inorganic bases, preferably the alkali metal hydroxides, carbonates, hydrides, amides and alkoxides, for example, sodium ethoxide, sodium hydroxide, potassium hydroxide, potassium carbonate, sodium methoxide and the like.

The compounds of this invention are capable of forming acid addition salts with therapeutically acceptable acids. The acid addition salts are prepared by reacting the base form of the appropriate compound of formula I with one or more equivalents, preferably with an excess, of the appropriate acid in an organic solvent, for example, ether (i.e., diethyl ether) or an ethanol-ether mixture. These salts, when administered to a mammal, possess the same pharmacologic activities as the corresponding bases. For many purposes it is preferable to administered the salts rather than the base compounds. Examples of suitable acids to form these salts include: the common mineral acids, e.g., hydrohalic, sulfuric or phosphoric; the organic acids, e.g., formic, acetic, maleic, malic, citric, or tartaric acid; and acids which are sparingly soluble in body fluids and which impart slow-release properties to their respective salts, e.g., pamoic acid tannic acid or carboxymethyl cellulose. The addition salts thus obtained are the functional equivalent of the parent base compound in respect to their therapeutic use. Hence, these addition salts are included with in the scope of this invention and are limited only by the requirement that the acids employed in forming the salts be therapeutically acceptable.

Also included in this invention are the stereochemical isomers of the compounds of formula I which result from asymmetric centers contained therein.

Individual optical isomers, which might be separated by fractional crystallization of the diastereoisomeric salts thereof, for instance, salts with d- or l-tartaric acid or D-(+)-α-bromocamphor sulfonic acid, are also included.

The compounds of this invention of formula I or a therapeutically acceptable salt thereof are useful diuretic agents in a mammal upon oral or parenteral administration.

The compounds of formula I are shown to be effective diuretic agents in mammals by tests conducted in rats. An example of such a test for diuretic agents is described by J. R. Cummings et al., J. Pharm. Exp. Tharap., 414, 128(1960). In this test, the urine of the rats is collected for five hours, during which time food and water are withdrawn. Urine volumes as well as sodium, potassium and chloride ion concentrations are determined. The compounds of this invention exhibit a dose response dependency when they are orally administered in dosages ranging from 5 to 100 mg per kilogram of body weight. The following representative compounds of this invention are effective diuretic agents at oral dosages ranging from 5 to 25 mg per kilogram of body weight: [4a,10b-cis]2,3,4,4a,6,10b-hexahydro-3,6,6-trimethyl-1H-[2]benzopyrano[3,4-c]pyridine (Example 15), [4a,10b-cis]-2,3,4,4a,6,10b-hexahydro-3-methyl-6-phenyl-1H-[2]benzopyrano-[3,4-c]pyridine (Example 16), [4a,10b-cis]-2,3,4,4a,6,10b-hexahydro-3-methyl-6-(3-fluorophenyl)-1H-[2]benzopyrano[3,4-c]pyridine (Example 19), [4a,10b-cis]-2,3,4,4a,6,10b-hexahydro-6-(3-chlorophenyl)1H-[2]benzopyrano[3,4-c]pyridine (Example 49) and [4a,10b-trans]-2,3,4,4a,6,10b-hexahydro-6-phenyl-2,4-ethano-1H-[2]-benzopyrano[3,4-c]pyridine (Example 49).

When the compounds of formula I of this invention are used as diuretic agents in mammals, e.g., rats and dogs, they are used alone or in combination with pharmacologically acceptable carriers, the proportion of which is determined by the solubility and chemical nature of the compound, chosen route of administration and standard biological practice. For example, they are administered orally in solid form, e.g., capsule or tablet. They can also be administered orally in the form of suspensions or solutions or they can be injected parenterally. For parenteral administration they are used in the form of a sterile solution containing other solutes, for example, enough saline or glucose to make the solution isotonic.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets may be uncoated or they may be coated by known techniques so as to delay disintegration and absorption in the gastrointestinal tract and thereby provide a sustained action over a longer period.

The aqueous suspensions of the invention contain the active ingredient in admixture with one or more non-toxic pharmaceutical excipients known to be suitable in the manufacture of aqueous suspensions. Suitable excipients are, for example, methyl-cellulose, sodium alginate, gum acacia, lecithin and so forth. The aqueous suspensions may also contain one or more preservatives, one or more coloring agents, one or more flavouring agents and one or more sweetening agents.

Non-aqueous suspensions may be formulated by suspending the active ingredient in a vegetable oil, for example, arachic oil, olive oil, sesame oil, or coconut oil, or in a mineral oil, for example liquid paraffin, and the suspension may contain a thickening agent, for example beeswax, hard paraffin or cetyl alcohol. These compositions may also contain a sweetening agent, flavouring agent and antioxidant.

The dosage of the compounds of formula I of this invention as diuretic agents will vary with the form of administration and the particular compound chosen. Furthermore, it will vary with the particular host, as well as the age and condition of the host under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects. The effective diuretic amount of the compounds usually ranges from about 1.0 mg to about 500 mg per kilogram of body weight per day, although as aforementioned variations will occur. However, a dosage level that is in the range of from about 10 mg to about 300 mg per kilogram of body weight per day is employed most desirably in order to achieve effective results.

The antidepressant activity of the compounds of formula I, or their acid addition salts with therapeutically acceptable acids, is demonstrated in standard pharmacologic tests such as, for example, the tests described by F. Hafliger and V. Burckhart in "Psychopharmacological Agents", M. Gordon, Ed., Academic Press, New York and London, 1964, pp. 75–83.

More specifically, as noted in the latter reference, the antidepressant properties of a compound may be demonstrated by its capacity to antagonize the depressant effects of reserpine. Furthermore, it is well documented that reserpine in animals produces a model depression which can be used for detecting antidepressant properties. Accordingly, the compounds of the present invention antagonize reserpine effects in mice at doses ranging from about 1 to 50 mg per kilogram of body weight. The preferred compounds, [4a,10b-cis]-3-methyl-6-(3-nitrophenyl)-2,3,4,4a,6,10b-hexahydro-1H-[2]benzopyrano[3,4-c]pyridine (Example 17) and [4a,10b-trans]-2,3,4,4a,6,10b-hexahydro-6-phenyl-2,4-ethano-1H-[2]benzopyrano[3,4-c]pyridine (Example 49), antagonize reserpine effects at an i.p. dose level of 2 to 6 mg per kilogram of body weight.

In general, the compounds of this invention are most desirably administered at a concentration level that will generally afford effective results without causing any harmful or deleterious side effects and preferably at a level that is in range of from about 0.1 mg to about 100 mg per kilogram of body weight per day, although as aforementioned variations will occur. However, a dosage level that is in the range of from about 0.5 mg to about 50 mg per kilogram of body weight per day is most desirably employed in order to achieve effective results.

The antihypertensive effect of the compounds of formula I and their acid addition salts is demonstrated in standard pharmacological tests. For example, in tests conducted in the spontaneously hypertensive rat (SHR), such as described by R. Tabei et al., Clin. Pharmacol. Therap. 11, 269 (1970) or I. Vavra et al., Can. J. Physiol. Pharmacol., 51, 727 (1973). More specifically exemplified, a testing method such as described in the latter publication shows that the preferred compound [4a,10b-trans]-2,3,4,4a,6,10b-hexahydro-3,6,6-trimethyl-1H-[2]benzopyrano[3,4-c]pyridine (Example 36) causes a notable blood pressure decrease in the SHR at about four hours after a dose of 25 to 50 mg per kilogram of body weight perorally.

The compounds of formula I or their acid addition salts with therapeutically acceptable acids also exhibit anorexic activity in a mammal. A suitable test for appetite suppression is described by G. A. Heise in "Animal and Clinical Pharmacoloic Techniques in Drug Evaluation", Vol. I edited by J. H. Nodine and P. E. Siegler, Year Book Medical Publishers, Inc., Chicago, 1964, pp. 279–282. Rats are trained to consume food during a four hour period in the morning. Food consumption is measured at one and four hours after p.o. administration of the standard (d-amphetamine) or the test compound and compared with the consumption of food by control rats given the vehicle only. This testing method shows that the preferred compounds, [4a,10b-cis]-2,3,4,4a,6,10b-hexahydro-3-methyl-6-(4-fluorophenyl)-1H-[2]-benzopyrano[3,4-c]pyridine (Example 20), [4a,10b-cis]-2,3,4,4a,10b-hexahydro-6-(3-chlorophenyl)-3-methyl-1H-[2]benzopyrano[3,4-c]-pyridine (Example 31) and [4a,10b-cis]-2,3,4,4a,6,10b-hexahydro-6-(3-fluorophenyl)-1H-[2]benzopyrano[3,4-c]pyridine (Example 49), at oral doses of 20 to 40 mg per kilogram of body weight reduced food consumption in the rat.

The anticonvulsant activity of the compounds of formula I or their acid addition salts with therapeutically acceptable acids is demonstrated in a modification of the maximal electroshock seizure (MES) method described by F. M. Berger, Proc. Soc. Exp. Biol., 78, 277 (1951). Albino male mice weighing between 18–24 g are used Seizures are produced by applying through corneal electrodes a current of 30 milliamps for 0.2 second. The percent of mice which are protected from the tonic phase of the seizure are recorded for each dose. Several of the preferred compounds, for example, [4a,10b-cis]-2,3,4,4a,6,10b-hexahydro-3,6,6-trimethyl-1H-[2]-benzopyrano[3,4-c]pyridine (Example 15), [4a,10b-cis]-2,3,4,4a,6,10b-hexahydro-3-methyl-6-phenyl-1H-[2]benzopyrano[3,4-c]pyridine (Example 16) and [4a,10b-cis]-2,3,4,4a,6,10b-hexahydro-3-ethyl-6-phenyl-1H-[2]benzopyrano[3,4-c]pyridine (Example 50), protect mice against MES at a dose level of 18–24 mg per kilogram of body weight, i.p.

When the compounds of formula I of this invention are used as antidepressant, antihypertensive, anorexic or anticonvulsant agents in a mammal, they are formulated i.e., capsule, tablet, aqueous solutions or suspensions and non-aqueous suspensions and administered in a similar manner as described above for their use as diuretic agents.

PROCESSES

Useful and practical starting materials for the preparation of the compounds of this invention of formula I are the compounds of formula II

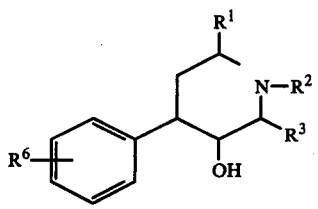

in which $R^1$, $R^3$ and $R^6$ are as defined herein and $R^2$ is lower alkyl, lower cycloalkyl(lower)alkyl or phenyl(lower)alkyl. The compounds of formula II can exist in the form of two isomers; formula IIa represents the cis isomer and formula IIb represents the trans isomer.

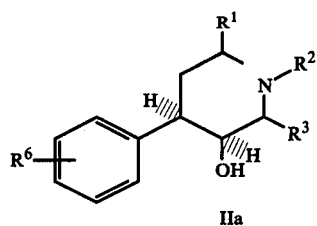

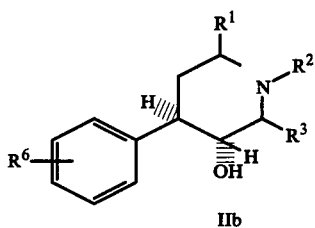

The starting materials of formula IIa are either known, for example, cis-1-methyl-4-phenyl-3-piperidinol, described by R. E. Lyle and W. E. Krueger, J. Org. Chem., 30, 394(1965), or they are prepared by the following process:

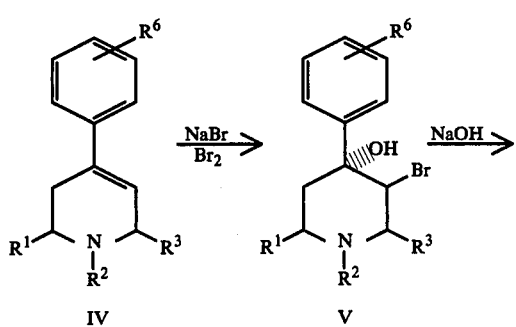

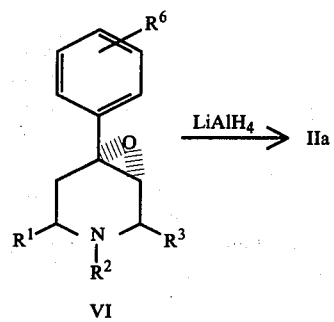

With reference to this process, described by R. E. Lyle and W. E. Krueger, supra, phenyl-1,2,3,6-tetrahydropyridines of formula IV are reacted with sodium bromide in the presence of bromine to obtain the bromohydrin of formula V. The bromohydrin is reacted with sodium hydroxide to obtain the epoxide of formula VI and reduction of the epoxide with lithium aluminum hydride gives the starting material of formula IIa. The phenyl-1,2,3,6-tetrahydropyridines of formula IV are either known or can be prepared according to the methods described by S. M. McElvain and J. C. Safranski, Jr., J. Amer. Chem. Soc., 72, 3134 (1950) and C. J. Schmidle and R. C. Mansfield, J. Amer. Chem. Soc., 78, 425 (1956).

The starting materials of formula IIb are readily prepared by reacting the phenyl-1,2,3,6-tetrahydropyridines of formula IV with diborane followed by treatment with sodium hydroxide according to the procedure of R. E. Lyle, et al., J. Org. Chem., 31, 4164 (1966).

The compounds of formula II, described above, can be transformed by conventional methods to obtain other compounds of formula II. For instance, the compound of formula II in which $R^1$, $R^3$ and $R^6$ are as defined herein and $R^2$ is phenylmethyl is hydrogenated using palladium on charcoal to obtain the corresponding compound of formula II in which $R^2$ is hydrogen Alternatively, the latter compound is obtained by reacting the compound of formula II in which $R^1$, $R^3$ and $R^6$ are as defined herein and $R^2$ is methyl with phenyl chloroformate in the presence of triethylamine and reacting the material formed with sodium hydroxide at about 220° C. to obtain the compound of formula II in which $R^2$ is hydrogen. The latter compound is reacted with a lower alkanoyl chloride, lower cycloalkylcarbonyl chloride, lower cycloalkyl(lower)alkanoyl chloride or phenyl(lower)alkanoyl chloride to obtain the corresponding amide intermediate and the intermediate is reduced with lithium aluminum hydride to obtain the corresponding compound of formula II in which $R^2$ is lower alkyl, lower cycloalkyl(lower)alkyl or phenyl(lower)alkyl.

The novel [2]benzopyrano[3,4-c]pyridine derivatives of this invention are readily and conveniently prepared by the following process:

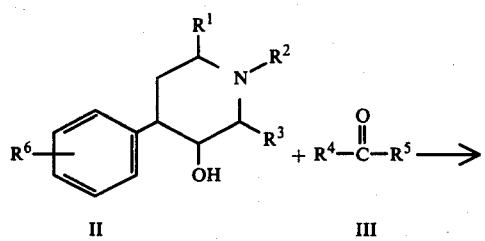
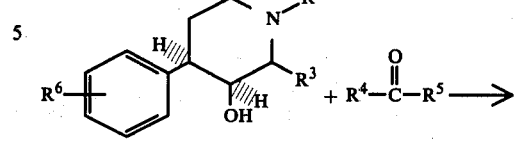
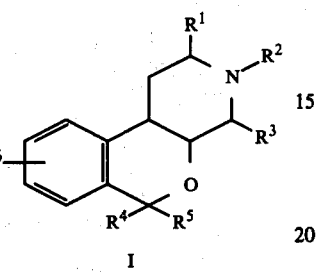
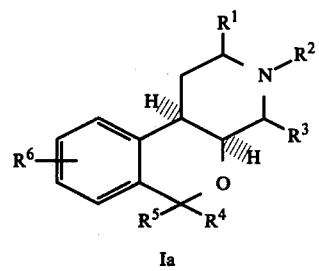

in which $R^1$, $R^3$, $R^4$, $R^5$ and $R^6$ are as defined herein and $R^2$ is lower alkyl, lower cycloalkyl(lower)alkyl or phenyl(lower)alkyl.

With reference to the above process, the starting material of formula II is condensed with one to five molar equivalents of the carbonyl compound of formula III in the presence of an acid catalyst to obtain the corresponding compound of formula I.

In practising the condensation (II + III → I) any solvent inert to the reaction conditions can be used. Suitable solvents include the cyclic ethers (i.e., tetrahydrofuran and the like) and the lower alkanols (i.e., methanol, ethanol and the like). Dioxane is especially convenient and practical as a solvent. The preferred acid catalyst for this condensation is anhydrous hydrogen bromide. The amount of acid catalyst is not especially critical and may range from 5 to 100 molar equivalents. The time of the reaction can range from 0.5 to 60 hours, preferably from one to 24 hours, at a temperature from −20° to 100° C. or the boiling point of the reaction mixture, preferably from 0° to 50° C. During the reaction it is advantageous to remove the water formed from the condensation. The addition of an anhydrous alkali-aluminum silicate (molecular sieves) to the reaction mixture is an effective means of removing the water.

The carbonyl compounds of formula III are aldehydes or ketones which are either known, for example, acetone, benzaldehyde, acetaldehyde or paraldehyde and cyclohexanecarboxaldehyde, or they can be prepared by known methods described in general organic chemistry textbooks. For example, a comprehensive review on the properties and preparation of such ketones and aldehydes may be found in "Rodd's Chemistry of Carbon Compounds", S. Coffey, Ed., Vol. Ic, 2nd ed., Elsevier Publishing Co., Amsterdam, 1965, pp. 1-99.

The compounds of formula I can exist as two isomers depending upon which isomer of formula II is used as starting material. For instance, the cis isomer of formula IIa gives the cis isomer of formula Ia, as illustrated by the following scheme.

Correspondingly, the trans isomer of formula IIb gives the trans isomer of formula Ib and is illustrated by the following scheme.

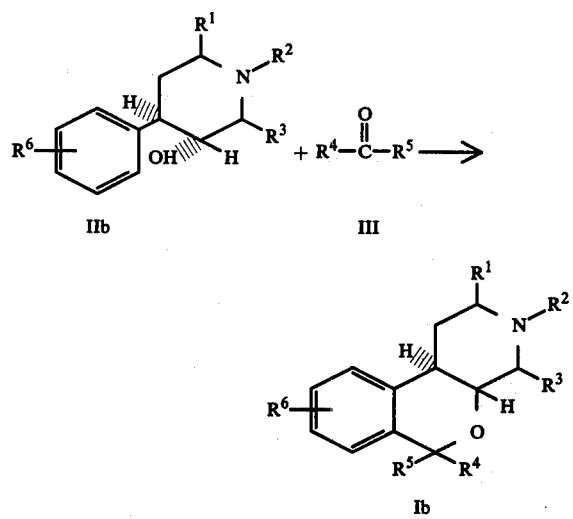

The compound of formula I, prepared as described above, can be further reacted to obtain other compounds of formula I.

For instance, the compound of formula I in which $R^1$, $R^3$, $R^4$, $R^5$ and $R^6$ are as defined herein and $R^2$ is phenylmethyl is reacted with hydrogen in the presence of a noble metal catalyst to obtain the corresponding compound of formula I in which $R^1$, $R^3$, $R^4$, $R^5$ and $R^6$ are as defined herein and $R^2$ is hydrogen. The hydrogenation is conveniently carried out in a solution consisting of an inert solvent, for example, benzene, toluene, methanol, ethanol and the like, in the presence of concentrated hydrochloric acid and a noble metal catalyst, preferably palladium or platinum on carbon, under an atmosphere of hydrogen at a pressure of about 20–80 p.s.i. and at a temperature of 0° to 50° C.

Alternatively, the compound of formula I in which $R^2$ is hydrogen can be prepared by the following processes. The compound of formula I in which $R^1$, $R^3$, $R^4$, $R^5$ and $R^6$ are as defined herein and $R^2$ is methyl is reacted with phenyl chloroformate in an inert solvent (i.e. methylene chloride, chloroform and the like) at a temperature of 20° to 80° C. for one to ten hours to obtain the corresponding intermediate having a phenoxycarbonyl group. Reaction of the latter intermediate with powdered sodium or potassium hydroxide at a temperature of 150° to 200° C. for about 10 to 30 minutes gives the corresponding compound of formula I in which $R^1$, $R^3$, $R^4$, $R^5$ and $R^6$ are as defined herein and $R^2$ is hydrogen.

The latter compound of formula I in which $R^2$ is hydrogen can be used to prepare other compounds of formula I.

For instance, the compound of formula I in which $R^2$ is hydrogen is reacted in an inert solvent with a lower alkanoyl chloride, bromide or iodide in the presence of a proton acceptor at a temperature of 10° to 50° C. for 10 to 40 hours to obtain the corresponding intermediate amide having a lower alkanoyl group.

The preferred proton acceptors are the organic amines, e.g. trimethylamine, triethylamine, N-methylmorpholine and the like. Preferred inert solvents for the reaction can be selected from methylene chloride, chloroform and the like. The intermediate amide is reduced with a complex metal hydride, preferably lithium aluminum hydride in a solvent selected from an ether or cyclic ether, preferably dioxane or tetrahydrofuran, at a temperature of 10° to 30° C. for about one to ten hours, to obtain the corresponding compound of formula I in which $R^2$ is lower alkyl. The compound of formula I in which $R^2$ is lower alkyl can also be obtained by reacting the corresponding compound of formula I in which $R^2$ is hydrogen with a lower alkyl halide wherein the halide is bromide, chloride or iodide in an inert solvent, such as methylene chloride, chloroform and the like, at a temperature from 40° C. to the boiling point of the reaction mixture for about 20 to 40 hours.

A further conversion of the compound of formula I in which $R^1$, $R^3$, $R^4$, $R^5$ and $R^6$ are as defined herein and $R^2$ is hydrogen comprises reacting the latter compound with about two to four molar equivalents of an ω-halo(lower)alkanoyl halide wherein each of the halogen atoms is selected from chlorine, bromine and iodine in the presence of a molar excess of a proton acceptor, preferably an organic base (i.e., triethylamine, N-ethylmorpholine and the like) in an inert organic solvent (i.e., methylene chloride, chloroform and the like) at a temperature from 10° to 50° C. for about 20 to 40 hours to obtain the corresponding halo-amide intermediate. Reaction of the latter intermediate with two to ten molar equivalents of ammonia, lower alkylamine or di(lower)alkylamine in the presence of two to six molar equivalents of a proton acceptor, preferably an inorganic base (i.e., sodium or potassium hydroxide, in a lower alkanol (i.e., methanol, ethanol and the like) at about 10° to 40° C. for about 10 to 50 hours yields the corresponding amino, lower alkylamino or di(lower)alkylamino alkanoyl intermediate. Reduction of the latter intermediate with a complex metal hydride gives the corresponding compound of formula I in which $R^1$, $R^3$, $R^4$, $R^5$ and $R^6$ are as defined herein and $R^2$ is amino(lower)alkyl, lower alkylamino(lower)alkyl or di(lower)alkylamino(lower)alkyl. Examples of suitable complex metal hydrides are lithium aluminum hydride, lithium aluminum hydride-aluminum chloride, aluminum hydride-aluminum chloride, diborane and sodium borohydride-aluminum chloride. Lithium aluminum hydride is preferred. Suitable solvents for the reduction include the dialkyl ethers or cyclic alkyl ethers, for example, diethyl ether, dioxane, tetrahydrofuran and the like. Tetrahydrofuran is the preferred solvent. The reduction is conveniently carried out at 0° to 30° C. for 10 to 30 hours.

The following examples illustrate further this invention.

EXAMPLE 1

1-Methyl-4-phenyl-4-piperidinol

Anhydrous ether (1900 ml) is placed, under nitrogen, in a previously dried 5 liter 3-necked flask fitted with dropping funnel, reflux condenser and magnetic stirrer. Lithium (28.4 g, 4.1 g. at.) is added together with 20 ml bromobenzene (20 ml). The mixture is heated at reflux temperature until a reaction commences. Heating is discontinued and a total of 312 g. (2.0 moles) bromobenzene is added dropwise during 0.5 hour. The mixture is stirred for a further 3 hours and the remaining traces of lithium are removed. The solution is cooled to 0° C. and 1-methyl-4-piperidone (161 g, 1.42 moles) is added over a 0.5 hour period. The mixture is stirred for a further 2 hours at room temperature, cooled to 0° C. and water (500 ml) is added. The mixture is transferred to a separating funnel. Methylene chloride is added to redissolve the precipitate which formed and the aqueous layer is extracted with ether. The combined ether extracts are dried over $Na_2SO_4$, evaporated and crystallized from methylene chloride-pentane to give the title compound, mp 110°–112° C. (S. M. Elreain and J. C. Safranski, Jr., supra, reported bp 128°–130° C./0.9mm).

In the same manner but replacing 1-methyl-4-piperidone with an equivalent amount of 8-methyl-8-azabicyclo[3.2.1]oct-3-one or 10-propyl-10-azabicyclo[4.3.1]dec-3-one, 8-methyl-3-phenyl-8-azabicyclo[3.2.1]octan-3-ol, mp 160°–161° C. [described by A. C. Cope and A. A. D'Addieco, J. Amer. Chem. Soc., 73, 3419(1951)] and 10-propyl-3-phenyl-10-azabicyclo[4.3.1]dec-3-ol are obtained.

EXAMPLE 2

1-Methyl-4-(3-methylphenyl)-4-piperidinol

To a layer of magnesium (24.3 g) covered with dry ether, a solution of m-bromotoluene (171 g, 1 mole) in dry ether (500 ml) is added under an atmosphere of nitrogen. After the addition, the mixture is heated at reflux for an hour, cooled to 0° C. and a solution of 1-methyl-4-piperidone (108 g, 950 mmoles) is added dropwise to the mechanically stirred mixture. The mixture is heated at reflux for 3 hours and allowed to stand at room temperature overnight. The suspension is cooled (<5°), 10% ammonium chloride solution is added and the mixture is extracted with ether. The combined extracts are dried ($MgSO_4$) and evaporated. The residue is crystallized from hexane to give the title compound, mp 86°–90° C.

In the same manner but replacing m-bromotoluene with an equivalent amount of p-bromotoluene or m-chlorobromobenzene, 1-methyl-4-(4-methylphenyl)-4-piperidinol, mp 122°–125° C. and 1-methyl-4-(3-chlorophenyl)-4-piperidinol are obtained.

EXAMPLE 3

1-Methyl-4-phenyl-1,2,3,6-tetrahydropyridine, IV

A solution of 1-methyl-4-phenyl-4-piperidinol (60.0 g, 0.314 moles, described in Example 1) in concentrated hydrochloric acid (180 ml, 2.16 moles) is heated with stirring at 100° C. for 4 hours. The resulting brown solution is evaporated to dryness and the buff residue is crystallized from isopropanol to give the title compound as the hydrochloride salt, mp 250°-252° C. (S. M. Elvain and J. C. Safranski, Jr., supra, reported mp 248°-250° C.

In the same manner but replacing hydrochloric acid with an equivalent amount of hydrobromic acid, the hydrobromide salt, mp 217°-218° C., of the title compound is obtained.

In the same manner but replacing 1-methyl-4-phenyl-4-piperidinol with an equivalent amount of 8-methyl-3-phenyl-8-azabicyclo[3.2.1]octan-3-ol (described in Example 1), 10-propyl-3-phenyl-10-azabicyclo[4.3.1]dec-3-ol (described in Example 1), 1-methyl-4-(3-methylphenyl)-4-piperidinol (described in Example 2), 1-methyl-4-(4-methylphenyl)-4-piperidinol (descibed in Example 2) or 1-methyl-4-(3-chlorophenyl)-4-piperidinol (described in Example 2), the following compounds of formula IV are obtained, respectively: 8-methyl-3-phenyl-8-azabicyclo[3.2.1]oct-2-ene, bp 128°-130° C./1.0 mm (A. C. Cope and A. A. D'Addieco, supra, reported bp 113°-115° C./0.45 mm), 10-propyl-3-phenyl-10-azabicyclo[4.3.1]dec-2-ene, 1-methyl-4-(3-methylphenyl)-1,2,3,6-tetrahydropyridine, bp 105°-110° C./0.4mm, 1-methyl-4-(4-methylphenyl)-1,2,3,6-tetrahydropyridine maleate salt, mp 157°-159° C. and 1-methyl-4-(3-chlorophenyl)-1,2,3,6-tetrahydropyridine, bp 112°-117° C./0.3 mm.

EXAMPLE 4

The title compound of Example 3 is prepared by the following alternative process.

Methylamine hydrochloride (47.0g; 0.680 mole) and 37% aqueous formaldehyde (113.0 g; 1.37 moles) are stirred, with warming, until the mixture is homogenous. 2-Methyl-2-phenylethene (78.7 g; 0.667 mole) is added and with vigorous stirring, the mixture is heated for 1 hour at 90° C. and cooled to 50° C. Concentrated sulphuric acid (57.0 g; 0.570 mole) is slowly added and the mixture is stirred at 90° C. for 3 hours. The mixture is poured into water (500 ml) and extracted with benzene. The aqueous layer is basified with 50% sodium hydroxide solution and extracted with benzene. The benzene extract is dried over $Na_2SO_4$, evaporated and distilled to give the title compound of Example 3, bp 100°-125° C./0.5 mm (C. J. Schmidle and R. C. Mansfield, supra, reported bp 85-90/0.8mm).

In the same manner but replacing 2-methyl-2-phenylethene with an equivalent amount of 2-methyl-2-(3-methylphenyl)-ethene or 2-methyl-2-(4-fluorophenyl)-ethene, the following compounds of formula IV are obtained, 1-methyl-4-(3-methylphenyl)-1,2,3,6-tetrahydropyridine, bp 110°-120° C./1.0 mm and 1-methyl-4-(4-fluorophenyl)-1,2,3,6-tetrahydropyridine, bp 110°-125° C./5 mm.

In the same manner but replacing methylamine hydrochloride with an equivalent amount of N-(phenylmethyl)amine hydrochloride, 1-phenylmethyl-4-phenyl-1,2,3,6-tetrahydropyridine, bp 148°-175° C./0.1 mm, is obtained.

EXAMPLE 5

1-Methyl-3-bromo-4-phenyl-4-piperidinol, V

1-Methyl-4-phenyl-1,2,3,6-tetrahydropyridine hydrobromide (110.0 g, 0.434 mole, described in Example 3) is dissolved in water (1250 ml). A solution of sodium bromide (128.0 g, 1.24 moles) and bromine (70.0 g, 0.440 mole) in water (1000 ml) is added dropwise with stirring to the above solution over a period of 1 hour. The mixture is concentrated under reduced pressure to half its original volume. The precipitate is isolated by filtration and recrystallized from glacial acetic acid to give the title compound as the hydrobromide salt, mp 191°-192° C. (R. E. Lyle and W. E. Krueger, supra, reported mp 195°-197° C.).

In the same manner but replacing 1-methyl-4-phenyl-1,2,3,6-tetrahydropyridine with an equivalent amount of 1-phenylmethyl-4-phenyl-1,2,3,6-tetrahydropyridine (described in Example 4) or 1-methyl-4-(3-methylphenyl)-1,2,3,6-tetrahydropyridine (described in Example 4), 1-phenylmethyl-3-bromo-4-phenyl-4-piperidinol, mp 113°-114° C., and 1-methyl-3-bromo-4-(3-methylphenyl)-4-piperidinol hydrobromide, mp 199°-200° C., are obtained.

EXAMPLE 6

3-Methyl-6-phenyl-7-oxa-3-azabicyclo[4.1.0]heptane, VI

A solution of 1-methyl-3-bromo-4-phenyl-4-piperidinol hydrobromide (4.10 g; 11.7 mmoles, described in Example 5) in water (5 ml) is cooled to 0°-5° C. Cold 10% aqueous sodium hydroxide solution (10 ml; 25 mmoles) is added dropwise with vigorous mechanical stirring, over a period of ten minutes. The solution is stirred for 30 min. and potassium carbonate is added to the solution at a temperature below 10° C. When the solution is saturated the solids are collected by filtration and crystallized from hexane at −70° C. to give the title compound, mp 44°-45° C. (R. E. Lyle and W. E. Krueger, supra, reported mp 43°-45° C.).

EXAMPLE 7

3-Methyl-6-(4-methylphenyl)-7-oxa-3-azabicyclo[4.1.0]heptane, VI

1-Methyl-4-(4-methylphenyl)-1,2,3,6-tetrahydropyridine maleate (5.0 g, 16.4 mmoles, described in Example 3) is suspended in water (60 ml) and a solution of sodium bromide (5.15 g, 49.9 mmoles) and bromine (0.84 ml) in water (50 ml) is added dropwise to the cooled mixture (<5° C.). The reaction mixture is stirred for 15 min., potassium carbonate (20 g) is added followed by chloroform (100 ml) and a solution of sodium hydroxide pellets (680 mg) in water (10 ml). After stirring vigorously for 15 min., the layers are separated and the aqueous solution is extracted with chloroform. The combined extracts are washed with brine, dried ($MgSO_4$) and evaporated. The residue is triturated with pentane to give the title compound, mp 124°-125.5° C.

In the same manner but replacing 1-methyl-4-(4-methylphenyl)-1,2,3,6-tetrahydropyridine with an equivalent amount of 1-methyl-4-(4-fluorophenyl)-1,2,3,6-tetrahydropyridine (described in Example 4) or 1-methyl-4-(3-methylphenyl)-1,2,3,6-tetrahydropyridine (described in Example 4), 6-(4-fluorophenyl)-3-methyl-7-oxa-3-azabicyclo[4.1.0]heptane, mp 46°-50° C. and 3-methyl-6-(3-methylphenyl)-7-oxa-3-azabicyclo[4.1.0]heptane are obtained respectively.

EXAMPLE 8 cis-1-Methyl-4-phenyl-3-piperidinol, IIa

A solution of 3-methyl-6-phenyl-7-oxa-3-azabicyclo[4.1.0]-heptane (1.00 g; 5.30 mmoles, described in Example 6) in anhydrous ether (10 ml) is added dropwise, with stirring to a slurry of lithium aluminum hydride (0.50 g, 13.2 mmoles) in anhydrous ether (50 ml). The mixture is stirred for 4 hours at room temperature. Excess lithium aluminum hydride is decomposed by slow addition of water (10 ml). The white precipitate is filtered and washed with ether. The combined ether layers are dried over potassium chloride and evaporated. The white solid residue is dried to give the title compound, mp 95°–97° C. (R. E. Lyle and W. E. Krueger, supra, reported mp 95°–97° C.).

In the same manner but replacing 3-methyl-6-phenyl-7-oxa-3-azabicyclo[4.1.0]heptane with an equivalent amount of 6-(4-fluorophenyl)-3-methyl-7-oxa-3-azabicyclo[4.1.0]heptane (described in Example 7), 3-methyl-6-(4-methylphenyl)-7-oxa-3-azabicyclo[4.1.0]heptane (described in Example 7) or 3-methyl-6-(3-methylphenyl)-7-oxa-3-azabicyclo[4.1.0]heptane (described in Example 7), cis-1-methyl-4-(4-fluorophenyl)-3-piperidinol, mp 93°–97° C., cis-1-methyl-4-(4-methylphenyl)-3-piperidinol maleate, mp 191°–194° C., and cis-1-methyl-4-(3-methylphenyl)-3-piperidinol oxalate, mp 168.5°–170.5° C., are obtained respectively.

EXAMPLE 9 cis-4-Phenyl-3-piperidinol, IIa

A solution of cis-1-methyl-4-phenyl-3-piperidinol (10.3 g, 53.8 mmoles, described in Example 8), methylene chloride (250 ml), triethylamine (12.0 g, 118 mmoles) and phenyl chloroformate (33.6 g, 215 mmoles) is heated at reflux for 16 hours. The mixture is cooled, ether is added and the mixture is filtered. Hexane is added to the filtrate and a pale yellow solid precipitates on standing. The precipitate is crystallized from benzene-hexane to give 1-phenyloxycarbonyl-4-phenyl-3-phenyloxycarbonyloxypiperidine, mp 153°–154° C.

The latter compound (1.0 g, 2.4 mmoles) is heated at reflux for 1 hr with anhydrous potassium carbonate (1.2 g) in methanol (40 ml). The mixture is concentrated under reduced pressure. The residue is dissolved in methylene chloride, dried (MgSO$_4$) and evaporated to give a brown oil which solidified. The solid is crystallized from benzene-hexane to give 1-methoxycarbonyl-4-phenyl-3-piperidinol, mp 139°–140° C.

The latter compound (5.0 g, 12 mmoles) is mixed with pulverised sodium hydroxide pellets (5.0 g, 125 mmoles) and the mixture is heated at 220° C. for 10 min. The melt is cooled, boiling water (50 ml) is added and the mixture is stirred until a clear solution is obtained. The cold solution is extracted with methylene chloride. The combined extracts are washed with brine, dried (MgSO$_4$) and evaporated. The residue (718 mg) is dissolved in boiling methylene chloride and the solution is added to an acetone solution of maleic acid (470 mg, 4.05 mmoles). The precipitate is filtered to afford a white solid which is crystallized from methanol-ether to give the title compound, as the maleate salt, mp 190°–190.5° C.

EXAMPLE 10 cis-1-Cyclopropylmethyl-4-phenyl-3-piperidinol, IIa cis-4-Phenyl-3-piperidinol (9.0 g, 50.8 mmoles, described in Example 9) is dissolved in methylene chloride (200 ml) and a 30% solution of sodium hydroxide (100 ml) is added. Cyclopropanecarboxylic acid chloride (5.72 g, 55.0 mmoles) is added dropwise to the cooled solution (10° C.) and stirring is continued for 15 minutes. The organic phase is separated, washed with brine, dried (MgSO$_4$) and evaporated. The residue is crystallized from ethyl acetate-ether to give cis-1-cyclopropylcarbonyl-4-phenyl-3-piperidinol, mp 175°–177° C.

In the same manner but replacing cyclopropanecarboxylic acid chloride with an equivalent amount of phenylacetyl chloride, cis-1-phenylacetyl-4-phenyl-3-piperidinol, mp 128°–129° C., is obtained.

cis-1-Cyclopropylcarbonyl-4-phenyl-3-piperidinol (10.01 g, 41.1 mmoles, described above) is suspended in dry tetrahydrofuran (250 ml) and added dropwise to a suspension of lithium aluminum hydride (5.0 g, 94.7 mmoles) in tetrahydrofuran. The mixture is stirred at room temperature for 2 hours. Water (60 ml) is added slowly to the cooled reaction mixture, followed by aqueous sodium hydroxide (60 ml, 3N). The gelatinous precipitate is removed by filtration and the filtrate evaporated. The solid residue is dissolved in methylene chloride, washed with brine, dried (MgSO$_4$) and evaporated. The residue is crystallized from hexane to give the title compound, mp 98°–100° C.

In the same manner but replacing cis-1-cyclopropylmethyl-4-phenyl-3-piperidinol with an equivalent amount of cis-1-phenylacetyl-4-phenyl-3-piperidinol, cis-1-(2-phenylethyl)-4-phenyl-3-piperidinol, mp 94°–97° C., is obtained.

EXAMPLE 11 trans-1-Methyl-4-phenyl-3-piperidinol, IIb

1-Methyl-4-phenyl-1,2,3,6-tetrahydropyridine (21.2 g; 122 mmoles, described in Example 3) and sodium borohydride (7.40 g, 195 mmoles) are dissolved in dried redistilled diglyme (100 ml). The solution is cooled, with stirring, under nitrogen and maintained at 0° C. during dropwise addition of a solution of boron trifluoride etherate (32 ml; 250 mmoles) in diglyme (15 ml). When the addition is complete, the mixture is stirred for 1.5 hours at room temperature. Water (10 ml) is added followed by 6N sodium hydroxide solution (30 ml). The temperature is raised to 50° C. followed by dropwise addition of 30% hydrogen peroxide solution (30 ml, 260 mmoles) over a period of 1 hour. Conc. hydrochloric acid (30 ml) is added, and the solvents are evaporated. The residue is redissolved in water and the evaporation is repeated. The residue is dissolved in water, basified with potassium carbonate solution, and the free base is extracted with ether. The extract is dried (Na$_2$SO$_4$), evaporated, and the residual yellow oil is distilled under reduced pressure. The material distilling at 115°–128° C./0.1 mm is crystallized from hexane to give the title compound, mp 78°–79.5° C. (R. E. Lyle et al, supra, reported mp 82°–84° C.).

In the same manner but replacing 1-methyl-4-phenyl-1,2,3,6-tetrahydropyridine with an equivalent amount of 1-methyl-4-(3-chlorophenyl)-1,2,3,6-tetrahydropyridine (described in Example 3) or 1-phenylmethyl-4-phenyl-1,2,3,6-tetrahydropyridine (described in Example 4), trans-1-methyl-4-(3-chlorophenyl)-3-piperidinol, bp 122°–135° C./0.1 mm and maleate salt mp 127°–128° C.; and trans-1-phenylmethyl-4-phenyl-3-piperidinol, mp 100°–101° C.; are obtained, respectively.

EXAMPLE 12 trans-8-Methyl-3-phenyl-8-azabicyclo[3.2.1]ectan-2-ol; IIb

A solution of 8-methyl-3-phenyl-8-azabicyclo[3.2.1]-oct-2-ene (44.4 g, 222 mmoles, described in Example 3) in tetrahydrofuran (225 ml) is added dropwise to a solution of diborane (1 mole) in tetrahydrofuran (500 ml). The solution is heated to reflux for 5 hours and allowed to stand at room temperature overnight. The solution is cooled to 0° C. and water (40 ml) is added. A 3N sodium hydroxide solution (190 ml) is added followed by a dropwise addition of a 30% solution of hydrogen peroxide (70 ml) to maintain reflux temperature. After completion of addition, the solution is heated at reflux for one hour and cooled. The solution is extracted with ether. The organic extract is washed with brine, dried (MgSO$_4$) and evaporated. A mixture of the residue and Raney nickel in ethanol (300 ml) is stirred for one hour. The mixture is filtered and the filtrate is evaporated. The residue is crystallized from ether to give the title compound, mp 115.5°–118° C.

In the same manner but replacing 8-methyl-3-phenyl-8-azabicyclo[3.2.1]oct-2-ene with an equivalent amount of 10-propyl-3-phenyl-10-azabicyclo[4.3.1]dec-2-ene (described in Example 3), trans-10-propyl-3-phenyl-10-azabicyclo[4.3.1]decan-2-ol is obtained.

EXAMPLE 13 trans-4-Phenyl-3-piperidinol, IIb

A solution of trans-1-phenylmethyl-4-phenyl-3-piperidinol (11.00 g, 51.5 mmoles, described in Example 11) in anhydrous ethanol (150 ml) containing concentrated hydrochloric acid (5 ml) is hydrogenated over 10% palladium on charcoal under 50 p.s.i. at 50° C. for 8 hours. The catalyst is removed by filtration over diatomaceous earth and the filtrate is evaporated. The residue is triturated with isopropanol and crystallized from methanol-ether to give the title compound, isolated as the hydrochloride salt, mp 233°–235° C.

EXAMPLE 14 trans-1-(2-Phenylethyl)-4-phenyl-3-piperidinol; IIb

Phenylacetyl chloride (13.6 g, 88 mmoles) is added dropwise to a stirring solution of trans-4-phenyl-3-piperidinol hydrochloride (19.0 g, 84.1 mmoles, described in Example 13), 0.90 M aqueous sodium hydroxide (200 ml) and methylene chloride (150 ml). The resulting emulsion is stirred at 10° C. for another 15 minutes. The methylene chloride layer is separated, washed with brine, (dried (MgSO$_4$) and evaporated. The residue is crystallized from isopranol-hexane to give trans-1-phenylacetyl-4-phenyl-3-piperidinol, mp 135°–136° C.

The latter compound (20.0 g, 67.7 mmoles) is suspended in dry tetrahydrofuran (200 ml) and added dropwise to a cold (5° C.) solution of lithium aluminum hydride (13.5 g, 350 mmoles) in tetrahydrofuran (300 ml). This mixture is stirred at room temperature overnight. Water (100 ml) is added slowly to the cooled mixture and addition is followed by aqueous sodium hydroxide (100 ml, 3N). The white precipitate is removed by filtration and the filtrate is washed with brine, dried (MgSO$_4$) and evaporated. The residue is crystallized from hexane to give the title compound, mp 115°–119° C.

In the same manner but replacing phenylacetyl chloride with an equivalent amount of cyclopropylcarbonyl chloride, trans-1-cyclopropylmethyl-4-piperidinol hydrochloride, mp 228°–230° C., is obtained.

EXAMPLE 15

[4a,10b-cis]-2,3,4,4a,6,10b-Hexahydro-3,6,6-trimethyl-1H-[2]benzopyrano[3,4-c]pyridine; 1 ($R^1$, $R^3$ and $R^6$ = H and $R^2$, $R^4$ and $R^5$ = $CH_3$)

A mixture of the compound of formula II, cis-1-methyl-4-phenyl-3-piperidinol (7.25 g, 37.9 mmoles, described in Example 8), in dioxane (80 ml) and molecular sieves type 4A is cooled to 0° C. Hydrogen bromide is bubbled through the mixture and when the initial precipitate redissolved, the compound of formula III, acetone (1 ml, 18 mmoles), is added. The mixture is warmed to room temperature. Hydrogen bromide is slowly bubbled in for 16 hours and during this time two further 1 ml aliquots of acetone are added, accompanied each time by a further quantity of molecular sieves. The mixture is filtered through glass wool, and under cooling aqueous potassium carbonate is added until the solution is alkaline. Dilute hydrochloric acid is added to bring the pH to 3. On standing a white precipitate forms and is filtered off. The filtrate is extracted with ether and the aqueous solution is evaporated. The residue is mixed with aqueous potassium carbonate and extrated with ether. The organic extract is washed with brine and dried (Na$_2$SO$_4$) to give the title compound.

Hydrogen bromide is slowly bubbled into a solution of the title compound in ether until no further precipitate forms. The precipitate is collected and crystallized from ethanol-pentane to give the title compound as the hydrobromide salt, mp 300° C. A solution of maleic acid in acetone is added to a solution of the title compound in ether. The crystals are collected and recrystallized from isopropanol-ether to give the title compound as the maleate salt, mp 148°–148.5° C.

In the same manner but replacing acetone with an equivalent amount of 3-pentanone, 3-hexanone, pentanal or cyclobutylmethanal, the following compounds of formula I are obtained respectively: [4a,10b-cis]-2,3,4,4a,6,10b-hexahydro-6,6-diethyl-3-methyl-1H-[2]benzopyrano[3,4-c]pyridine, [4a,10b-cis]-2,3,4,4a,6,10b-hexahydro-6-ethyl-3-methyl-6-propyl-1H-[2]benzopyrano[3,4-c]pyridine, [4a,10b-cis]-2,3,4,4a,6,10b-hexahydro-6-butyl-3-methyl-1H-[2]benzopyrano[3,4-c]pyridine and [4a,10b-cis]-2,3,4,4a,6,10b-hexahydro-6-cyclobutyl-3-methyl-1H-[2]benzopyrano[3,4-c]pyridine.

In the same manner but replacing cis-1-methyl-4-phenyl-3-piperidinol with an equivalent amount of trans-10-propyl-3-phenyl-10-azabicyclo[4.3.1]decan-2-ol (described in Example 12), [4a,10b-trans]-2,3,4,4a,6,10b-hexahydro-2,4-butano-6,6-dimethyl-3-propyl-1H-[2]benzopyrano[3,4-c]pyridine is obtained.

EXAMPLE 16

[4a,10b-cis]-2,3,4,4a,6,10b-Hexahydro-3-methyl-6-phenyl-1H-[2]benzopyrano[3,4-c]pyridine; 1 ($R^1$, $R^3$, $R^4$ and $R^6$ = H, $R^2$ = $CH_3$ and $R^5$ = $C_6H_5$)

The compound of formula II, cis-1-methyl-4-phenyl-3-piperidinol (5.00 g, 26.1 mmoles, described in Example 8), is dissolved in dioxane (60 ml). Hydrogen bromide is bubbled through the cold solution until all of the precipitate dissolves. The compound of formula III, benzaldehyde (2.70 g, 25.5 mmoles) is added to the solution and hydrogen bromide addition is continued for 3 hours. The mixture is poured into a mixture of ice and water. The white precipitate is filtered and dissolved in methylene chloride. The solution is dried (MgSO₄) and evaporated. The residue is crystallized from methylene chloride-ether to give the title compound as the hydrobromide salt, mp 263°-264° C.

By following a procedure selected from Example 15 or 16 using the appropriate compounds of formula II and III, other compounds of formula I are obtained.

Examples of such compounds of formula I are listed as products in Table I together with the appropriate compounds of formula II and III used for the preparation of the compound of formula I. In each case the compound of formula II is noted by the number of the example in which it is prepared.

Table 1

| EXAMPLE | COMPOUND OF FORMULA III $R^4$ | $R^5$ | NO. OF THE EXAMPLE IN WHICH STARTING MATERIAL OF FORMULA II IS PREPARED | PRODUCT:[(PREFIX LISTED BELOW)-2,3,4,4a,6,10b-HEXAHYDRO-1H-[2]BENZO-PYRANO[3,4-c]-PYRIDINE PREFIX |
|---|---|---|---|---|
| 17 | H | 3-nitrophenyl | 8 | [4a,10b-cis]-3-methyl-6-(3-nitrophenyl), maleate salt, mp 182-184.5° C |
| 18 | H | CH₃ | 8 | [4a,10b-cis]-3,6-dimethyl, HBr salt, mp 280-283° C |
| 19 | H | 3-fluorophenyl | 8 | [4a,10b-cis]-3-methyl-6-(3-fluorophenyl), HBr salt, mp 265-267° C |
| 20 | H | 4-fluorophenyl | 8 | [4a,10b-cis]-3-methyl-6-(4-fluorophenyl), HBr salt, mp 170-175° C |
| 21 | H | 2-fluorophenyl | 8 | [4a,10b-cis]-3-methyl-6-(2-fluorophenyl), HBr salt, mp 268-269° C |
| 22 | H | 2-chlorophenyl | 8 | [4a,10b-cis]-3-methyl-6-(2-chlorophenyl), HBr salt, mp 271-273° C |
| 23 | H | 3-methylphenyl | 8 | [4a,10b-cis]-3-methyl-6-(3-methylphenyl), HBr salt, mp 274-276° C |
| 24 | H | cyclohexyl | 8 | [4a,10b-cis]-3-methyl-6-cyclohexyl, HBr salt, mp 135-138° C |
| 25 | H | 4-chloro-3-trifluoromethylphenyl | 8 | [4a,10b-cis]-3-methyl-6-(4-chloro-3-trifluoromethyl-phenyl), maleate salt, mp 203.5-205.5° C |
| 26 | H | 4-chloro-3-trifluoromethylphenyl | 8 | [4a,10b-cis]-6-(4-chloro-3-trifluoromethyl-phenyl)-3,8-dimethyl, maleate salt mp 192-195° C |
| 27 | H | 2-trifluoromethylphenyl | 8 | [4a,10b-cis]-3-methyl-6-(2-trifluoromethylphenyl), maleate salt, mp 226-228° C |
| 28 | H | 3-trifluoromethylphenyl | 8 | [4a,10b-cis]-3-methyl-6-(3-trifluoromethylphenyl), HBr salt, mp 202.5-204° C |
| 29 | H | phenyl | 8 | [4a,10b-cis]-8-fluoro-3-methyl-6-phenyl, HBr salt mp 115-190° C |
| 30 | H | 3-fluorophenyl | 8 | [4a,10b-cis]-3,9-dimethyl 6-(3-fluorophenyl), HBr salt, mp 255-257° C |
| 31 | H | 3-chlorophenyl | 8 | [4a,10b-cis]-3-methyl-6-(3-chlorophenyl), HBr salt, mp 280-281° C |
| 32 | H | 3-trifluoromethylphenyl | 8 | [4a,10b-cis]-3,8-dimethyl 6-(3-trifluoromethyl-phenyl), maleate salt, mp 198-199° C |
| 33 | H | 3-fluorophenyl | 8 | [4a,10b-cis]-3,8-dimethyl-6-(3-fluorophenyl), HBr salt, mp 170-174° C |
| 34 | H | 3-fluorophenyl | 10 | [4a,10b-cis]-3-cyclopropylmethyl-6-(3-fluorophenyl), HBr salt, mp 240-242° C |
| 35 | H | 3-fluorophenyl | 10 | [4a,10b-cis]-3-(2-phenylethyl)-6-(3-fluorophenyl), 2-naphthalene sulfonate salt, mp 227-229° C |
| 36 | CH₃ | CH₃ | 11 | [4a,10b-trans]-3,6,6-trimethyl, HBr salt, mp 238-242° C |
| 37 | H | 2-chlorophenyl | 11 | [4a,10b-trans]-3-methyl-6-(2-chlorophenyl), HBr salt, mp 196-199° C |
| 38 | H | 2-methylphenyl | 11 | [4a,10b-trans]-3-methyl-6-(2-methylphenyl), maleate salt, mp 170-180° C |
| 39 | H | phenyl | 11 | [4a,10b-trans]-3-methyl-6-phenyl, maleate salt, mp 172-175° C |
| 40 | H | phenyl | 11 | [4a,10b-trans]-3-phenylmethyl-6-phenyl: isomer A, mp 134-135° C, isomer B, mp 100-104° C |

Table 1-continued

| EXAMPLE | COMPOUND OF FORMULA III R⁴ R⁵ | | NO. OF THE EXAMPLE IN WHICH STARTING MATERIAL OF FORMULA II IS PREPARED | PRODUCT:[(PREFIX LISTED BELOW)-2,3,4,4a,6, 10b-HEXAHYDRO-1H-[2]BENZO-PYRANO[3,4-c]-PYRIDINE PREFIX |
|---|---|---|---|---|
| 41 | H | phenyl | 12 | [4a,10b-trans]-3-methyl-6-phenyl-2,4-ethano; isomer A, HBr salt, mp 280–282° C and isomer B, HBr salt, mp > 300° C |
| 42 | H | 3-fluorophenyl | 12 | [4a,10b-trans]-3-methyl-6-(3-fluorophenyl)-2,4-ethano, HBr salt, mp 275–277° C |
| 43 | H | 2-methylphenyl | 14 | [4a,10b-trans]-3-cyclopropylmethyl-6-(2-methylphenyl), HBr salt, mp 241–242° C |
| 44 | H | 2-methylphenyl | 14 | [4a,10b-trans]-3-(2-phenylethyl)-6-(2-methylphenyl), 2-naphthalene sulfonate salt, mp 208–213° C |
| 45 | H | phenyl | 14 | [4a,10b-trans]-3-cyclopropylmethyl-6-phenyl, maleate salt, mp 184–187° C |
| 46 | H | 3-fluorophenyl | 14 | [4a,10b-trans]-3-(2-phenylethyl)-6-(3-fluorophenyl), HBr salt, mp 241–245° C |
| 47 | H | phenyl | 14 | [4a,10b-trans]-3-(2-phenylethyl)-6-phenyl, HBr salt, mp 223–227° C |

EXAMPLE 48

[4a,10b-trans]-2,3,4,4a,6,10b-Hexahydro-6-phenyl-1H-[2]-benzopyrano[3,4-c]pyridine, 1 ($R^1$, $R^2$, $R^3$, $R^4$ and $R^6$ = H and $R^5$ = $C_6H_5$)

A mixture of isomers of [4a,10b-trans]-2,3,4,4a,6,10b-hexahydro-3-phenylmethyl-6-phenyl-1H-[2]benzopyrano[3,4-c]pyridine (26.8 g, 75.5 mmoles, described in Example 40) is dissolved in a benzeneethanol 1:1 (700 ml) solvent mixture and concentrated hydrochloric acid (10 ml) is added. This solution is hydrogenated over 10% palladium on charcoal (20 g) catalyst at 50 p.s.i. at 25° C. for 42 hours. The catalyst is removed by filtration on diatomaceous earth and the filtrate is evaporated. The residue is dissolved in methylene chloride, washed with a solution of potassium carbonate and evaporated.

The residue is subjected to chromatography on silica gel using methanol as eluent. The appropriate fractions are combined and evaporated. The residue is dissolved in methylene chloride-ether and hydrogen bromide is added. The precipitate is collected and crystallized from isopropanol-ether to give the title compound as the hydrobromide salt, mp 249°–254° C.

EXAMPLE 49

[4a,10b-cis]-2,3,4,4a,6,10b-Hexahydro-6-phenyl-1H-[2]benzopyrano[3,4-c]pyridine;1 ($R^1$, $R^2$, $R^3$, $R^4$ and $R^6$ = H and $R^5$ = $C_6H_5$)

A solution of [4a,10b-cis]-2,3,4,4a,6,10b-hexahydro-3-methyl-6-phenyl-1H-[2]-benzopyrano[3,4-c]pyridine hydrobromide (10.0 g, 52.2 mmoles, described in Example 16) in methylene chloride is washed with aqueous potassium carbonate solution and evaporated. The residue is dissolved in methylene chloride (70 ml) and phenyl chloroformate (15.0 g, 96.3 mmoles) is added in small portions. The mixture is heated at reflux for 4 hr and evaporated. The residue is subjected to chromatography on a column of silica gel using methanol-chloroform (1:4). The eluates are evaporated and the residue is crystallized from methylene chloride-pentane to give [4a,10b-cis]-2,3,4,4a,6,10b-hexahydro-6-phenyl-1H-[2]benzopyrano[3,4-c]pyridine-3-carboxylic acid phenyl ester, mp 174°–175.5° C.

A mixture of the latter compound (5.00 g, 13.0 mmoles) and potassium hydroxide is ground in a mortar. The fine powder is thoroughly mixed and heated at 160°–175° C. for 15–20 minutes. The solid is cooled and triturated with water (400 ml). The suspension is extracted with methylene chloride. The extract is washed with brine, dried ($Na_2SO_4$) and evaporated. The residue is dissolved in ether and hydrogen bromide is added. The precipitate is collected and crystallized from isopropanol-ether to give the title compound as the hydrobromide salt, mp 260°–263° C.

In the same manner but replacing [4a,10b-cis]-2,3,4,4a,6,10b-hexahydro-3-methyl-6-phenyl-1H-[2]benzopyrano[3,4-c]pyridine with an equivalent amount of the title compound of Example 19, 31 or 41, the following compounds of formula I are obtained respectively: [4a,10b-cis]-2,3,4,4a,6,10b-hexahydro-6-(3-fluorophenyl)-1H-[2]-benzopyrano[3,4-c]pyridine hydrobromide, mp 251°–253° C.; [4a,10b-cis]-2,3,4,4a,6,10b-hexahydro-6-(3-chlorophenyl)-1H-[2]benzopyrano-[3,4-c]pyridine hydrobromide, mp 193°–197° C., and [4a,10b-trans]-2,3,4,4a,6,10b-hexahydro-6-phenyl-2,4-ethano-1H-[2]benzopyrano-[3,4-c]pyridine hydrobromide, mp 299°–300° C.

EXAMPLE 50

[4a,10b-cis]-2,3,4,4a,6,10b-Hexahydro-3-ethyl-6-phenyl-1H-[2]benzopyrano[3,4-c]pyridine; 1 ($R^1$, $R^3$, $R^4$ and $R^6$ = H, $R^2$ = $C_2H_5$ and $R^5$ = $C_6H_5$)

Acetyl chloride (2.52 g, 32.0 mmoles) is added dropwise to a solution of [4a,10b-cis]-2,3,4,4a,6,10b-hexahydro-6-phenyl-1H-[2]benzopyrano[3,4-c]pyridine hydrobromide (10.0 g, 29.0 mmoles, described in Example 49) and triethylamine (6.16 g, 61.0 mmoles) in methylene chloride (250 ml). The mixture is stirred overnight and ether is added until no further precipitate forms. The mixture is filtered and the filtrate is evaporated to give an oil which is dissolved in ether. The solution is washed with sodium bicarbonate solution, 0.2 N hydrochloric acid and water; dried over MgSO₄; and evaporated. The residue is crystallized from ether to give [4a,10b-cis]-2,3,4,4a,6,10b-hexahydro-3-acetyl-6-phenyl-1H-[2]benzopyrano[3,4-c]pyridine, mp 153°–156° C.

A solution of the latter compound (6.4 g, 20.8 mmoles) in tetrahydrofuran (100 ml) is added dropwise to a slurry of lithium aluminum hydride (0.79 g, 20.8 mmoles) in tetrahydrofuran (200 ml). The mixture is stirred for four hours, water (70 ml) is added, followed by 2 N sodium hydroxide (20 ml). The mixture is extracted with ether and the combined extracts are washed with brine, dried over MgSO₄, and evaporated. The residue is subjected to chromatography on silica gel using methanol-chloroform (1:4) and the eluates are evaporated. The residue in an acetone solution is mixed with maleic acid and ether is added. The crystals are collected and recrystallized from methanolether to give the title compound as the maleate salt, mp 165°–170° C.

In the same manner but replacing acetyl chloride with an equivalent amount of butanoyl bromide, 3-methylbutanoyl chloride or hexanoyl chloride, [4a,10b-cis]-2,3,4,4a,6,10b-hexahydro-3-butyl-6-phenyl-1H-[2]benzopyrano[3,4-c]pyridine, [4a,10b-cis]-2,3,4,4a,6,10b-hexahydro-3-(3-methylbutyl)-6-phenyl-1H-[2]benzopyrano[3,4-c]-pyridine and [4a,10b-cis]-2,3,4,4a,6,10b-hexahydro-3-hexyl-6-phenyl-1H-[2]benzopyrano[3,4-c]pyridine are obtained.

The title compound is also prepared using the following process.

A solution of [4a,10b-cis]-2,3,4,4a,6,10b-hexahydro-6-phenyl-1H-[2]benzopyrano[3,4-c]pyridine (7.20 g, 27.2 mmoles, described in Example 49) and ethyl iodide (20.0 g, 128 mmoles) in methylene chloride (300 ml) is heated at reflux overnight. The mixture is concentrated to about 100 ml and ether is added until no further precipitate forms. The solvents are decanted. The oily precipitate is dissolved in a solution of methylene chloride and aqueous potassium carbonate is added. The solution is extracted with methylene chloride. The combined extracts are washed with brine, dried (MgSO₄) and evaporated. The residue is dissolved in acetone and maleic acid is added. Ether is added to the warm solution and the mixture is allowed to stand at room temperature for 2 days. The white solid is collected and crystallized from methanol-ether to give the title compound as the maleate salt, mp 188°–190° C.

EXAMPLE 51

[4a,10b-cis]-2,3,4,4a,6,10b-Hexahydro-3-[3-(dimethylamino)propyl]-6-phenyl-1H-[2]benzopyrano[3,4-c]pyridine; 1 ($R^1$, $R^3$, $R^4$ and $R^6$ = H, $R^2$ = (CH₂)₃N(CH₃)₂ and $R^5$ = C₆H₅)

3-Chloropropionyl chloride (8.6 ml, 80.9 mmoles) is added to a solution of [4a,10b-cis]-2,3,4,4a,6,10b-hexahydro-6-phenyl-1H-[2]benzopyrano[3,4-c]pyridine (9.80 g, 36.8 mmoles, described in Example 49) and triethylamine (12.2ml) in methylene chloride (350 ml). The mixture is stirred at room temperature overnight. Aqueous sodium bicarbonate is added and the mixture is stirred for 15 minutes. The organic layer is separated, washed with water, brine, dried (Na₂SO₄) and evaporated to give [4a,10b-cis]-2,3,4,4a,6,10b-hexahydro-3-[3-chloro-1-oxo-propyl]-6-phenyl-1H-[2]benzopyrano[3,4-c]pyridine.

The latter compound (10.22 g, 28.7 mmoles) in methanol (50 ml) is added dropwise to a solution of dimethylamine hydrochloride (7.22 g, 87.4 mmoles) in ethanol (350 ml). The mixture is stirred at room temperature for 24 hours and evaporated. The residue is dissolved in methylene chloride (400 ml), washed with brine, dried (Na₂SO₄) and evaporated to give [4a,10b-cis]-2,3,4,4a,6,10b-hexahydro-3-[3-dimethylamino-1-oxopropyl]-6-phenyl-1H-[2]-benzopyrano[3,4-c]pyridine.

The latter compound (8.44 g, 24.1 mmoles) is dissolved in dry tetrahydrofuran (100 ml) and the solution is added to a suspension of lithium aluminum hydride (7.5 g) in tetrahydrofuran (200 ml). The mixture is stirred at room temperature for 18 hours. The reaction mixture is cooled in an ice bath and water (30 ml) is added followed by a solution of 2N sodium hydroxide (40 ml). The mixture is filtered and the filtrate is evaporated. The residue is dissolved in methylene chloride. The solution is washed with water, brine, dried and evaporated. The residue is dissolved in methylene chloride (60 ml) and a solution of maleic acid (4.20 g) in acetone (30 ml) is added. Ether is added and the precipitate is collected and crystallized from methanol-ether to give the title compound as the maleate salt, mp 188°–191° C.

In the same manner but replacing [4a,10b-cis]-2,3,4,4a,6,10b-hexahydro-6-phenyl-1H-[2]benzopyrano[3,4-c]pyridine with the other compounds of formula I described in Example 49, the following compounds of formula I are obtained: [4a,10b-cis]-2,3,4,4a,6,10b-hexahydro-3-[3-(dimethylamino)propyl]-6-(3-fluorophenyl)-1H-[2]-benzopyrano[3,4-c]pyridine, [4a,10b-cis]-2,3,4,4a,6,10b-hexahydro-3-[3-(dimethylamino)propyl]-6-(3-chlorophenyl)-1H-[2]benzopyrano-[3,4-c]pyridine and [4a,10b-cis]-2,3,4,4a,6,10b-hexahydro-3-[3-(dimethylamino)propyl]-6-phenyl-2,4-ethano-1H-[2]benzopyrano[3,4-c]-pyridine.

In the same manner but replacing 3-chloropropionyl chloride with an equivalent amount of 5-chloropentanoyl chloride and replacing dimethylamine with an equivalent amount of ammonia, butylamine or N-ethyl-N-methylamine, the following compounds of formula I are obtained respectively: [4a,10b-cis]-2,3,4,4a,6,10b-hexahydro-3-(5-aminopentyl)-6-phenyl-1H-[2]benzopyrano[3,4-c]pyridine, [4a,10b-cis]-2,3,4,4a,6,10b-hexahydro-3-[5-(butylamino)pentyl]-6-phenyl-1H-[2]benzopyrano[3,4-c]-pyridine and [4a,10b-cis]-2,3,4,4a,6,10b-hexahydro-3-[5-(N-ethyl-N-methylamino)pentyl]-6-phenyl-1H-[2]benzopyrano[3,4-c]pyridine.

We claim:
1. [4a,10b-cis]-2,3,4,4a,6,10b-Hexahydro-3,6,6-trimethyl-1H-[2]benzopyrano[3,4-c]pyridine.

2. [4a,10b-cis]-2,3,4,4a,6,10b-Hexahydro-3-methyl-6-phenyl-1H-[2]benzopyrano[3,4-c]pyridine.

3. [4a,10b-cis]-2,3,4,4a,6,10b-Hexahydro-3-methyl-6-(3-nitrophenyl)-1H-[2]benzopyrano[3,4-c]pyridine.

4. [4a,10b-cis]-2,3,4,4a,6,10b-Hexahydro-3-methyl-6-(3-fluorophenyl)-1H-[2]benzopyrano[3,4-c]pyridine.

5. [4a,10b-cis]-2,3,4,4a,6,10b-Hexahydro-3-methyl-6-(4-fluorophenyl)-1H-[2]benzopyrano[3,4-c]pyridine.

6. [4a,10b-cis]-2,3,4,4a,6,10b-Hexahydro-3-methyl-6-(2-fluorophenyl)-1H-[2]benzopyrano[3,4-c]pyridine.

7. [4a,10b-cis]-2,3,4,4a,6,10b-Hexahydro-3-methyl-6-(4-chloro-3-trifluoromethyl-phenyl)-1H-[2]benzopyrano[3,4-c]-pyridine.

8. [4a,10b-cis]-2,3,4,4a,6,10b-Hexahydro-3,8-dimethyl-6-(4-chloro-3-trifluoromethyl-phenyl)-1H-[2]benzopyrano[3,4-c]pyridine.

9. [4a,10b-cis]-2,3,4,4a,6,10b-Hexahydro-3-methyl-6-(2-trifluoromethylphenyl)-1H-[2]benzopyrano[3,4-c]pyridine.

10. [4a,10b-cis]-2,3,4,4a,6,10b-Hexahydro-3-methyl-6-(3-trifluoromethylphenyl)-1H-[2]benzopyrano[3,4-c]pyridine.

11. [4a,10b-cis]-2,3,4,4a,6,10b-Hexahydro-3-methyl-6-(3-chlorophenyl-1H-[2]benzopyrano[3,4-c]pyridine.

12. [4a,10b-cis]-2,3,4,4a,6,10b-Hexahydro-3,8-dimethyl-6-(3-trifluoromethylphenyl)-1H-[2]benzopyrano[3,4-c]pyridine.

13. [4a,10b-trans]-2,3,4,4a,6,10b-Hexahydro-3,6,6-trimethyl-1H-[2]benzopyrano[3,4-c]pyridine.

14. [4a,10b-trans]-2,3,4,4a,6,10b-Hexahydro-3-(2-phenylethyl)-6-phenyl-1H-[2]benzopyrano[3,4-c]pyridine.

15. [4a,10b-trans]-2,3,4,4a,6,10b-Hexahydro-6-phenyl-1H-[2]benzopyrano[3,4-c]pyridine.

16. [4a,10b-cis]-2,3,4,4a,6,10b-Hexahydro-6-phenyl-1H-[2]benzopyrano[3,4-c]pyridine.

17. [4a,10b-cis]-2,3,4,4a,6,10b-Hexahydro-6-(3-fluorophenyl)-1H-[2]benzopyrano[3,4-c]pyridine.

18. [4a,10b-cis]-2,3,4,4a,6,10b-Hexahydro-6-(3-chlorophenyl)-1H-[2]benzopyrano[3,4-c]pyridine.

19. [4a,10b-cis]-2,3,4,4a,6,10b-Hexahydro-6-phenyl-2,4-ethano-1H-[2]benzopyrano[3,4-c]pyridine.

20. [4a,10b-cis]-2,3,4,4a,6,10b-Hexahydro-3-ethyl-6-phenyl-1H-[2]benzopyrano[3,4-c]pyridine.

21. A process for preparing a compound of formula I

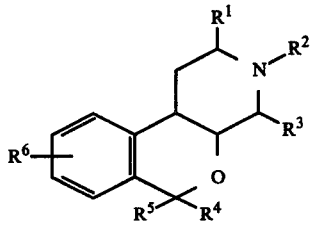

in which $R^1$ and $R^3$ are hydrogen or $R^1$ and $R^3$ together form a —$(CH_2)_n$— chain wherein n is an integer from 2 to 4; $R^2$ is hydrogen, lower alkyl, lower cycloalkyl(lower)alkyl, phenyl(lower)alkyl, amino(lower)alkyl, lower alkylamino(lower)alkyl or di(lower)alkylamino(lower)alkyl; $R^4$ is hydrogen or lower alkyl; $R^5$ is lower alkyl, lower cycloalkyl, phenyl or phenyl substituted with one or two substitutents selected from the group consisting of nitro, halo, lower alkyl and trifluoromethyl; and $R^6$ is hydrogen, halo or lower alkyl; or a therapeutically acceptable acid addition salt thereof comprising:
condensing a compound of formula II

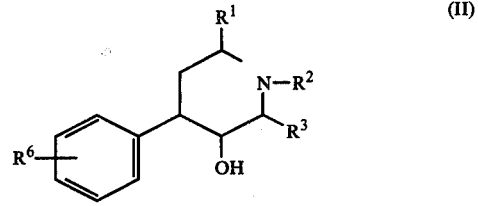

in which $R^1$ and $R^3$ are hydrogen, or $R^1$ and $R^3$ together form a —$(CH_2)_n$— chain wherein n is an integer from 2 to 4; $R^2$ is lower alkyl, lower cycloalkyl(lower)alkyl or phenyl(lower)alkyl and $R^6$ is hydrogen, halo or lower alkyl with a carbonyl compound of formula III

in which $R^4$ is hydrogen or lower alkyl and $R^5$ is lower alkyl, lower cycloalkyl, phenyl or phenyl substituted with one or two substituents selected from the group consisting of nitro, halo, lower alkyl and trifluoromethyl in the presence of an acid catalyst to obtain the corresponding compound of formula I in which $R^1$, $R^3$, $R^4$, $R^5$ and $R^6$ are as defined herein and $R^2$ is lower alkyl, lower cycloalkyl(lower)alkyl or phenyl(lower)alkyl; followed, when it is desired to obtain the corresponding compound at formula I in which $R^1$, $R^3$, $R^4$, $R^5$ and $R^6$ are as defined herein and $R^2$ is hydrogen, reducing said compound of formula I in which $R^1$, $R^3$, $R^4$, $R^5$ and $R^6$ are as defined herein and $R^2$ is the phenyl(lower)alkyl, phenylmethyl, with hydrogen in the presence of a noble metal catalyst, or by reacting said compound of formula I in which $R^1$, $R^3$, $R^4$, $R^5$ and $R^6$ are as defined herein and $R^2$ is the lower alkyl, methyl, with phenyl chloroformate followed by heating with powdered sodium or potassium hydroxide; and when it is desired to obtain the compound of formula I in which $R^1$, $R^3$, $R^4$, $R^5$ and $R^6$ are as defined herein and $R^2$ is amino(lower)alkyl, lower alkylamino(lower)alkyl or di(lower)alkylamino(lower)alkyl, reacting the compound of formula I in which $R^1$, $R^3$, $R^4$, $R^5$ and $R^6$ are as defined herein and $R^2$ is hydrogen with a compound of formula ω-halo(lower)alkanoyl halide wherein each of the halogen atoms is selected from chlorine, bromine and iodine in the presence of a proton acceptor to obtain the corresponding halo-amide, reacting said haloamide with ammonia, a lower alkylamine or a di(lower)alkylamine in the presence of a proton acceptor, to obtain the corresponding amino-amide and reducing said amino-amide with a complex metal hydride.

* * * * *